(12) United States Patent
Goshert

(10) Patent No.: US 6,723,099 B1
(45) Date of Patent: Apr. 20, 2004

(54) THREE SIDED TACK FOR BONE FIXATION

(75) Inventor: David R. Goshert, Pierceton, IN (US)

(73) Assignee: Biomet, Inc., Warsaw, IN (US)

( * ) Notice: Subject to any disclaimer, the term of this patent is extended or adjusted under 35 U.S.C. 154(b) by 30 days.

(21) Appl. No.: 10/035,515

(22) Filed: Nov. 8, 2001

(51) Int. Cl.[7] .......................... A61B 17/56; A61B 17/58; A61F 2/30
(52) U.S. Cl. .......................................... 606/72; 606/75
(58) Field of Search ............................. 606/61, 65, 70, 606/72, 73, 75, 76; 411/3, 4, 508, 509, 510, 913, 450, 452, 453, 456, 393, 402, 403, 410

(56) References Cited

U.S. PATENT DOCUMENTS

| | | | |
|---|---|---|---|
| 723,452 A | | 3/1903 | Estes |
| 1,103,542 A | | 7/1914 | Russell |
| 2,699,774 A | | 1/1955 | Livingston |
| 3,604,487 A | | 9/1971 | Gilbert |
| 4,454,875 A | | 6/1984 | Pratt et al. |
| 4,653,486 A | | 3/1987 | Coker |
| 4,728,238 A | * | 3/1988 | Chisholm et al. ........... 411/510 |
| 4,776,739 A | * | 10/1988 | Hamman ................... 411/510 |
| 4,973,211 A | * | 11/1990 | Potucek ..................... 411/452 |
| 5,120,168 A | * | 6/1992 | Padula ........................... 411/5 |
| 5,713,903 A | | 2/1998 | Sander et al. |
| 5,720,753 A | | 2/1998 | Sander et al. |
| 5,720,766 A | * | 2/1998 | Zang et al. ................. 606/232 |
| 5,797,714 A | * | 8/1998 | Oddenino ................... 411/508 |
| 5,813,810 A | * | 9/1998 | Izume ........................ 411/510 |
| 5,941,885 A | | 8/1999 | Jackson |
| 5,961,520 A | * | 10/1999 | Beck, Jr. et al. .............. 606/72 |
| 5,971,987 A | | 10/1999 | Huxel et al. |
| 6,001,100 A | * | 12/1999 | Sherman et al. .............. 606/72 |
| 6,004,349 A | * | 12/1999 | Jackson ....................... 623/17 |
| 6,062,788 A | * | 5/2000 | Ying-Feng .................. 411/480 |
| 6,099,530 A | * | 8/2000 | Simonian et al. ............. 606/75 |
| 6,264,677 B1 | * | 7/2001 | Simon et al. ................ 606/232 |
| 6,302,885 B1 | * | 10/2001 | Essiger ........................ 606/72 |
| 2002/0120274 A1 | * | 8/2002 | Overaker et al. ............. 606/72 |
| 2002/0156476 A1 | * | 10/2002 | Wilford ....................... 606/72 |

OTHER PUBLICATIONS

Macropore ™ Surgical Tacks and Drivers, http:\www.macropore.com/prod04.htm, Nov. 7, 2001.

* cited by examiner

Primary Examiner—Eduardo C. Robert
Assistant Examiner—Anuradha Ramana
(74) Attorney, Agent, or Firm—Harness, Dickey & Pierce, P.L.C.

(57) ABSTRACT

A surgical tack for bone fixation having a body portion with barbs on the outside of the body portion to fixedly engage a bone structure, and a head portion to assist in implantation of the surgical tack. The tack also includes fins on the body portion to reduce implantation forces while not reducing the holding power of the surgical tack. The barbs extend from the fins to engage a bone structure and increase the holding force of the surgical tack. Additionally, a break-away portion is affixed to the head portion to engage an implantation device to assist an implantation of the surgical tack.

21 Claims, 4 Drawing Sheets

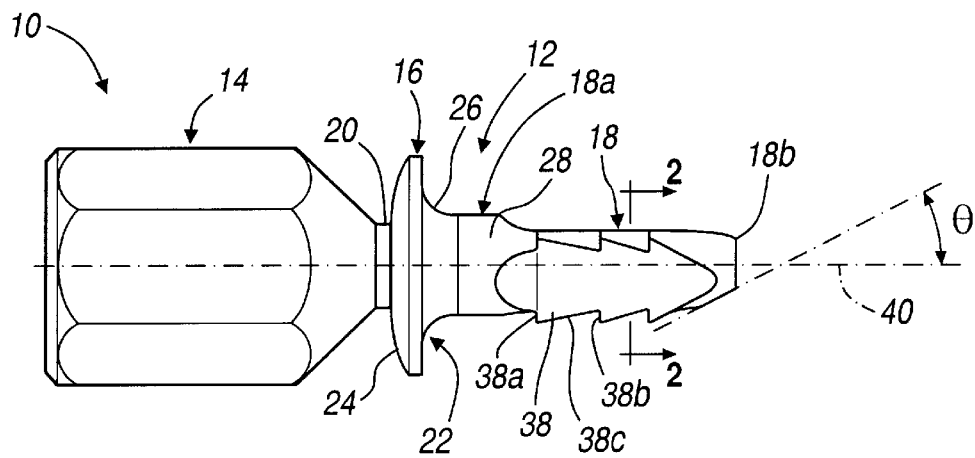
FIG.- 1
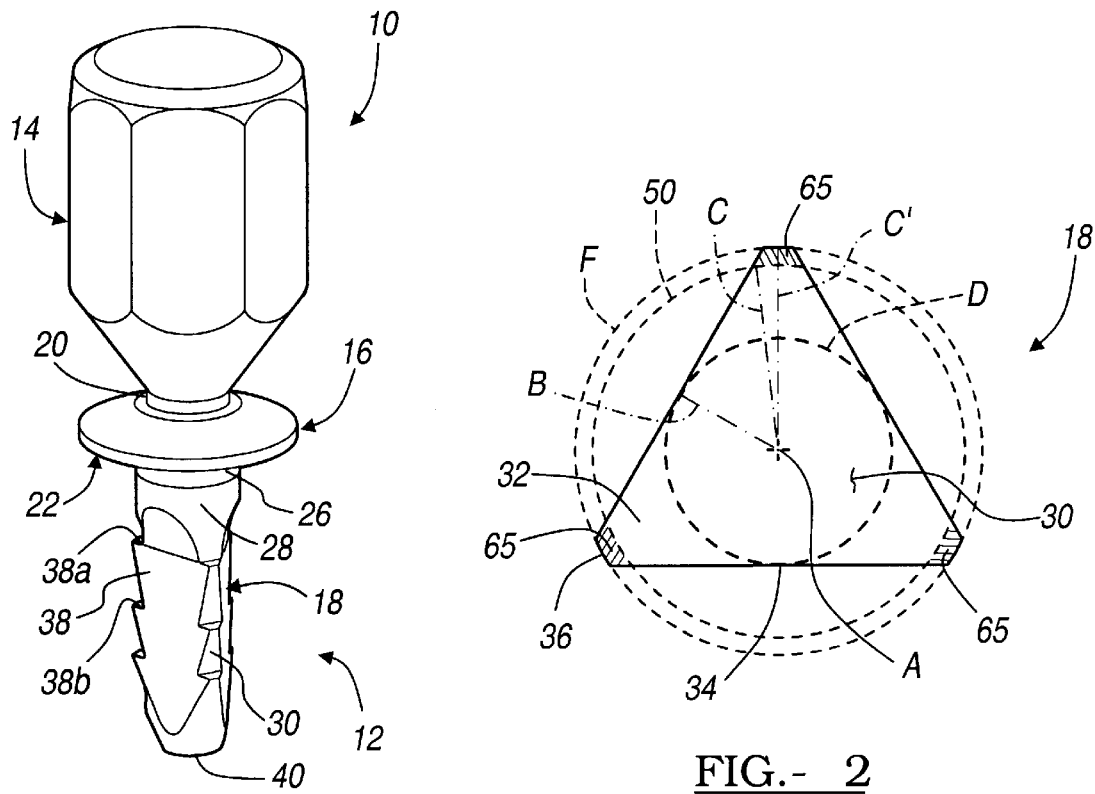
FIG.- 1a
FIG.- 2

THREE SIDED TACK FOR BONE FIXATION

FIELD OF THE INVENTION

The present invention relates generally to bone fixation devices and more particularly to bone fixation push pins or tacks.

BACKGROUND OF THE INVENTION

Bone structures in a human body, or other animals, may undergo degenerative processes which lead to weakening or an ultimate break of the bone structure. Additionally, a catastrophic event may cause a break or fracture in the bone structure. When such breaks occur, some kind of repair mechanism must generally be used to help the bone heal properly. Certain mechanisms include external fixation of the bone structure so that it can grow together in proper alignment. External fixation is fixation of the bone structure with a device placed on the outside of the derma. Other methods include internal fixation which include some mechanism placed subcutaneous to hold the bone structure in place while it heals.

Internal plate and bone fixation methods are generally known. Plates having a specific rigidity are mounted to bone structures using known fixture means. One known method of fixing a plate to a bone is using a surgical screw which is held in place through threads. These screws are inserted using a driver into a pilot hole that had been drilled into the bone. Additionally, surgical or orthopedic tacks are known to hold bone plates,in place. The tack is press fit into a pilot hole that was drilled into the bone structure. Generally, these bone tacks resemble hardware tacks. Known tacks generally included a head portion affixed to a proximal end of a tack body. The tack body has a generally sloping profile that terminates in a sharp point or relatively narrow distal end. These tacks may also include ribs that help hold the tack in place. Generally, however, the pilot hole for these tacks must be substantially equal to the greatest diameter of the tack body. If the pilot hole is not substantially equal to the width or diameter of the largest part of the tack body, great pressure must be used to insert the bone tack into the bone and hold it in place.

It is, therefore, desirable to have a bone tack that has an increased holding power without requiring the increased pressure to implant the bone tack into the bone structure. It is also desirable to decrease the resulting stress on the bone structure after implantation. When additional force is used to push a bone tack into a bone structure, greater trauma may arise than if a smaller force was used to insert a bone tack into the bone structure.

SUMMARY OF THE INVENTION

A first embodiment of the present invention includes a bone fixation tack which has a body which has a proximal end and a distal end wherein the tack is to be received in a bone structure. A head portion extends from the proximal end of the body. A removable member further extends from the head portion. Finally, a projection is operatively associated with the body portion to form a bone engaging area when implanted in the bone structure.

A second embodiment of the present invention includes a surgical fixation tack which has a tack portion having a first circumference and a proximal end and a distal end. A head portion extends from the proximal end of the tack portion. Finally, a plurality of fins extend from the tack portion and form a second circumference which is greater than the first circumference.

A third embodiment of the present invention includes a surgical tack that has a tack portion with a plurality of fins where the fins effectively reduce the surface area of the tack portion. A head portion extends from the tack portion. Finally, projections are operatively associated with the tack portion to help hold the tack portion in the structure.

The bone fixation tack according to the present invention has a generally circular interior cross section with a generally triangular total cross section. The triangular cross section provides a minimal resistance during the implantation of the bone fixation tack into a bone structure. After implantation, each point of the generally triangular cross section will provide resistance to extraction or unintended removal of the bone fixation tack from the bone structure into which it was implanted. Additionally, projections, such as barbs are formed on each of the points of the triangular cross section to also resist removal of the bone fixation tack. The head portion of the tack may also include an integrally formed insertion member which may be removed once the bone fixation tack has been affixed into the bone. Also, a plate through which the bone fixation tack will be inserted is disclosed to hold two portions of the bone relative to each other for a healing process.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 shows an elevational, view of a bone fixation tack including a break-off hex according to a first embodiment of the present invention;

FIG. 1a shows a perspective view of the bone fixation tack of FIG. 1;

FIG. 2 shows a cross-sectional view taken along line 2—2 of FIG. 1;

FIG. 4a is a detailed view of FIG. 4 taken about circle 4a;

DETAILED DESCRIPTION OF THE PREFERRED EMBODIMENTS

Figure 3:
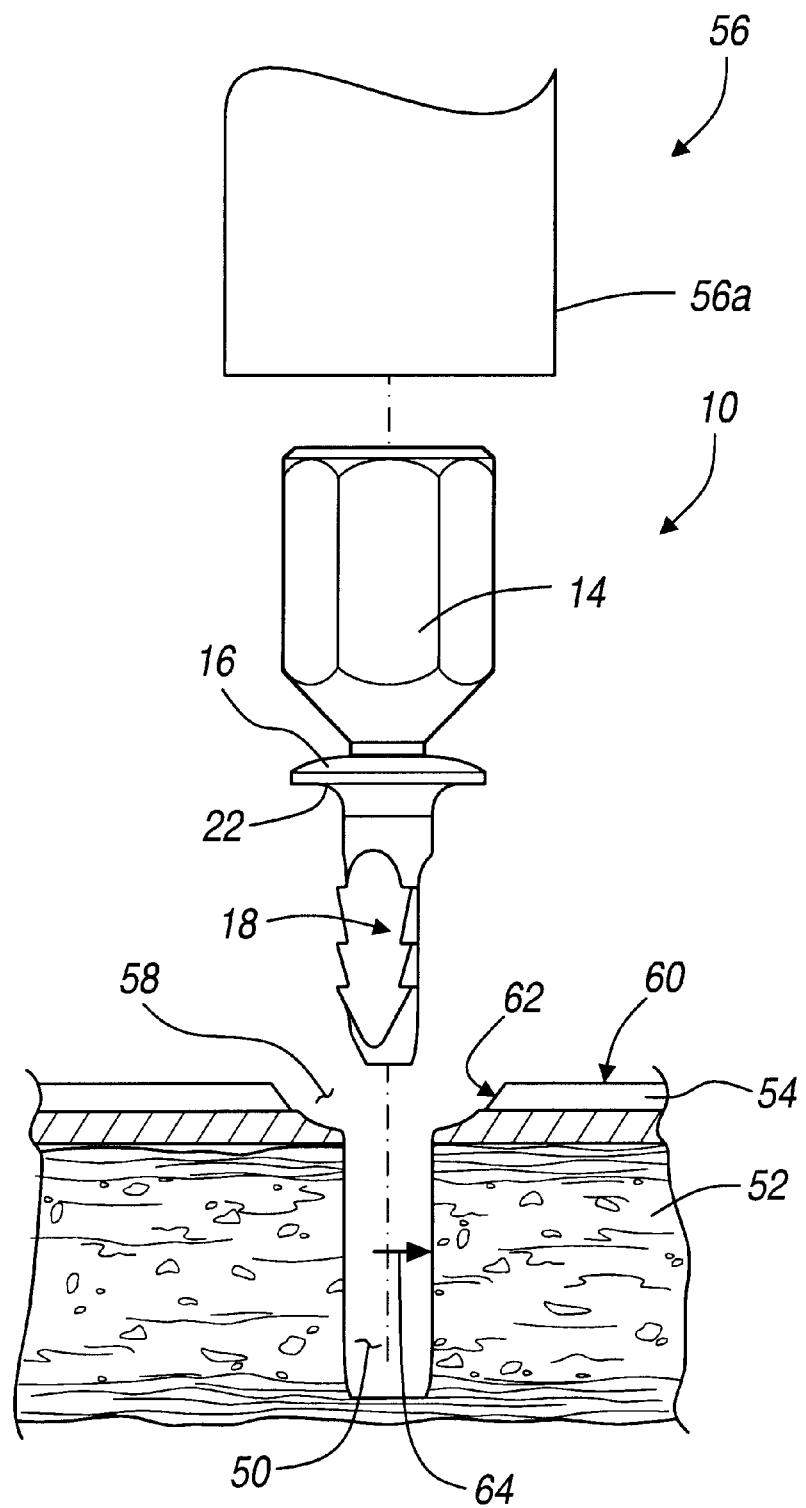
FIG. 3 is an exploded view of the insertion of a bone fixation tack into a bone structure through a bone plate according to a first embodiment of the present invention.

The following description of the preferred embodiment(s) is merely exemplary in nature and is in no way intended to limit the invention, its application, or uses. Additionally, exemplary measurements and ratios are given without intending to be bound to the specific measurements given and described.

With reference to FIGS. 1 and 1a, a first embodiment of a bone fixation device 10 is shown including a bone fixation tack 12 and a break-off hex driver 14. The bone fixation tack 12 includes a head portion 16 and a tack or body portion 18 where the body portion 18 is to be implanted into a bone structure of a patient. The body portion 18 has a proximal end 18a near head portion 16 and a distal end 18b. Break-off hex 14 includes a snap or break-away region 20 that is formed to be weaker than the surrounding area to facilitate the removal of the break-off hex 14 after the bone fixation tack 12 is implanted into the bone structure. The break-away region 20 extends between the break-off hex 14 and the head portion 16 and holds the bone fixation tack 12 to the break-off hex 14 during implantation of the bone fixation tack 12.

The head portion 16 includes an annular bottom surface 22 which is to be received into a bone fixation plate (shown at 54 in FIG. 3) for a flush fit with the bone fixation plate 54. The head portion 16 also includes a top surface 24 which is adapted to lie substantially flush with the bone fixation plate 54 once inserted. Directly below the bottom surface 22 is a collar region 26 which extends between the body portion 18 of the bone fixation tack 12 to the head portion 16. The collar region 26 gradually increases in diameter from the diameter of the body portion 18 to a diameter slightly less than the diameter of the head portion 16. This ensures a strong fixation between the body portion 18 and the head portion 16 of bone fixation tack 12.

Extending from the collar region 26 is a top or top portion 28 of the body portion 18. With continuing reference to FIG. 1 and further reference to FIG. 2, the body portion 18 includes a central region 30 and fins 32. Fins 32 are substantially equal to or greater than diameter to the top portion 28. Central region 30 includes a center point A and is generally circular having a radius B. For example, the radius B between center point A and interior edge 34 may be between about 0.01 and about 0.5 inches. A second radius or distance C is formed from center point A to an outside edge 36 of each fin 32. An exemplary length of distance C may be about 0.01 inches to about 1.0 inches. This configuration defines an inner circumference D, defined by radius B, smaller than an exterior circumference F, defined by distance C. It will be understood that the distance of radii B and C are exemplary only and may be any appropriate length depending upon the intended application.

Body portion 18 may be formed in several different ways. One method, for exemplary purpose only, is that fins 32 may be affixed to the central region 30. A circular central region, having substantially parallel sides such as a cylinder, may have affixed to it through a suitable means, such as welding, the fins 32. A second example of forming the body portion 18 is to view the central region 30 as an imaginary portion simply defining a central continuous circumference inside of fins 32. Such a structure is formed through providing a substantially cylindrical portion having a radius substantially equal to the distance C and grinding down three sides of the cylindrical portion. Grinding down three sides would produce the fins 32 and the body portion 18 having a generally triangular a cross section. Central region 30 would still be defined by a circumference with the radius being substantially defined by the distance B.

Each fin 32 also includes a projection or barb 38. The barbs 38 project and are formed on the outside edge 36 of fins 32. Barbs 38 resist the tendency of the bone fixation tack 12 to move backward out of a pilot hole formed in the bone structure. Barbs 38 have a distance from center point A greater than or equal to the distance C the outside edge of fins 32. Barbs 38 also include a structure to assist in implantation of the bone fixation tack 12 while resisting the removal of the fixation tack 12. In particular, a proximal edge 38a of the barb 38 nearest the proximal end 18a of the body portion 18 has a height above the fin 32 greater than a distal edge 38b of the barb 38, which is closest the distal end 18b of the body portion 18. In particular, the proximal edge 38a of the barb 38 would define radius C', the greatest radius of the body portion 18. Furthermore, an outer surface 38c of the barb 38 has an incline from the proximal edge 38a to the distal edge 38b. The proximal edge 38a has a height of about 0.001 inches to about 0.01 inches above the outside edge 36 of fin 32 which, for example, is about 0.001 inches to about 0.01 inches greater than distance C. The distal edge 38b is substantially planar with the outside edge 36 of fin 32, or a distance equal to distance C. Therefore, surface 38c would assist in the implantation of the bone fixation tack 12 while the proximal edge 38a will resist the removal of bone fixation tack 12.

Distal end 18b of the body portion 18 is narrower and has a smaller diameter than the top portion 28. A plane 40 parallel to center point A forms an angle of θ approximately 12–18 degrees from the outside edge 36 of fin 32. Angle θ allows the distal end 18b to be more easily implanted into the bone structure. This helps decrease the force necessary to begin the implantation of the bone fixation tack 12 into a surface. The distances C and C' may also increase from the distal end 18b to the proximal end 18a of the tack body 18 such that the fins 32 are sloped from the distal end 18b to the proximal end 18a, as are the barbs 38.

With continuing reference to FIG. 2 and to FIG. 3, an exploded view of the process of implanting bone fixation tack 12 is illustrated. A pilot hole 50 is first formed in the bone structure 52 to receive the bone fixation tack 12. The bone fixation tack 12 is then driven through a bone fixation plate 54 and into the pilot hole 50. A driver 56 having a first end 56a engages the break-off hex 14 to help hold bone fixation tack 12 during implantation. A bore 58 is formed in the bone fixation plate 54 to receive the bone fixation tack 12. Additionally, an upper surface 60 of the bone fixation plate 54 includes a recess 62 adapted to substantially receive bottom surface 22 of head portion 16. Pilot hole 50 has a radius 64 in between the length of radius B and radius C.

The bone fixation tack 12 has a first circumference or first effective circumference D which is the circumference of the internal area 30. The bone fixation tack 12 also has a second or outer circumference F defined by radius C which is the distance between the center point A and the outer surface 36 of each fin 32. It will be understood that other gradually increasing outer radii will be formed by the outer surface 38c of each barb 38. Pilot hole 50 may be any circumference between inner circumference D and outer circumference F. This allows for an engagement between fins 32 and the bone structure 52 while not requiring every portion of the outer surface of the bone fixation tack 12 to engage the bone structure 52. Implantation forces are substantially reduced when pilot hole 50 has a radius in between distance C and distance C'. Additionally, implantation forces, while maintaining an acceptable holding force, are optimized when the radius of the pilot hole 50 is, for example, between about 0.001 inches and 0.01 inches less than distance C'. With particular reference to FIG. 2, shaded areas 65 are defined by the area of the fin 32 between the radius 64 of the pilot hole 50 and the distance of radius C or outer circumference F. The bone engagement area 65 is the primary or only area of the bone fixation tack 12 that actually engages the bone structure 52 during implantation of the bone fixation tack 12. It will also be understood that barbs 38 extending from outer edge 36 of fin 32 are also engaging bone structure 52 and further resist removal of the bone fixation tack 12 due to the inverted incline of outer surface 38c. It will also be understood that the area of the bone engaging area 65 may be increased or decreased by altering the radius 64 of the pilot hole 50.

Figure 4:
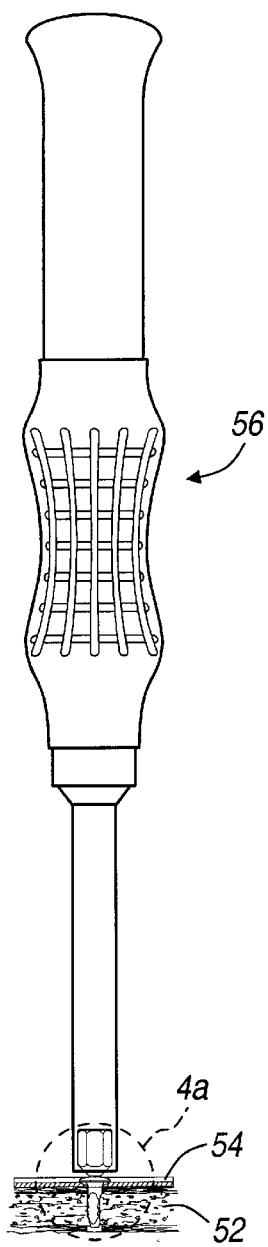
FIG. 4 is a elevational view of a bone fixation tack insertion instrument engaging a bone insertion tack through a bone fixation plate and bone structure according to the first embodiment of the present invention.
Figure 4A:
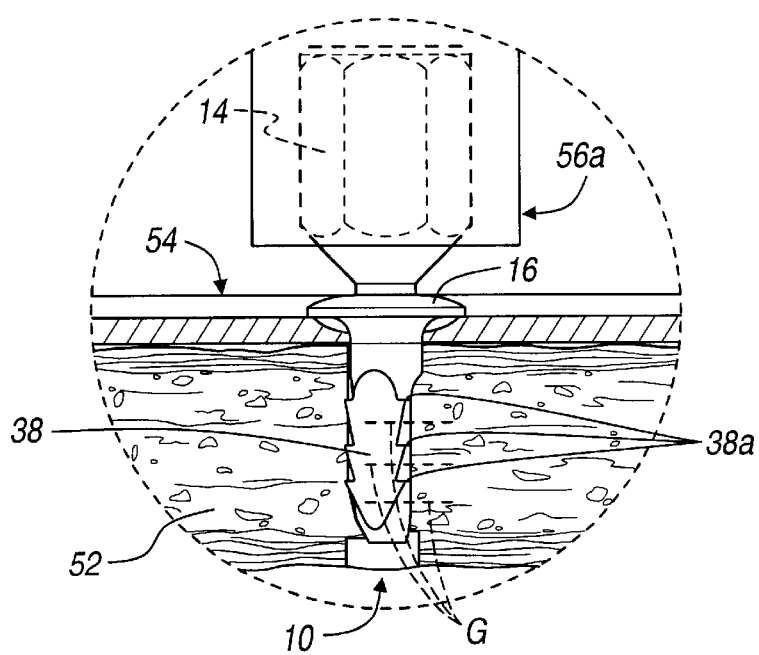

Turning to FIGS. 4 and 4a, bone fixation tack 12 is shown implanted into a bone structure 52. Driver 56 engages the break-off hex 14 of the bone fixation device 10 prior to breaking away the break-off hex 14. A hexagonal design of the break-off hex 14 ensures a tight fit of bone fixation device 10 with the driver 56. Also, the hexagonal design of the break-off hex 14 ensures that torque may be transmitted between the driver 56 and the bone fixation device 10. The bone fixation tack 12 is fit through the bone fixation plate 54 and into the bone structure 52. Head portion 16 is substantially received into the recess 62 of the bone fixation plate 54 to ensure that a profile over the bone fixation plate 54 is substantially flat so as to reduce irritation to the patient after implantation. Additionally, barbs 38 engage the bone structure 52 after implantation into the bone structure 52. Since the radius 64 of the pilot hole 50 is between distance C and distance C', only the portion of the barb 38 near the proximal edge 38a engages the bone structure 52. With particular reference to FIG. 4a, the bone fixation tack 12 is held in the bone structure 52 with a portion of the barb 38. The portion of the barb 38 between line G and the proximal edge 38a engages the bone structure 52. For example, this area may be represent about the upper forty percent of the barb 38.

Implantation of the bone fixation tack 12 into the bone structure 52 is generally achieved by pressing the bone fixation tack 12 in through the bone fixation plate 54 into the bone structure 52. Bone fixation device 10 is first placed in driver device 56 and held in place with the driver break-off hex 14. Pilot hole 50 is formed into the bone structure 52 using any suitable means. The surgeon then presses the bone fixation tack 12 into bone structure 52 through the bone fixation plate 54.

Since the radius 64 of the pilot hole 50 is less than radius C of the body portion 18, a certain amount of force is needed to press the bone fixation tack 12 into the pilot hole 50. Since only three bone engagement areas 65 of the fins 32, have a distance substantially greater than the radius 64 of the pilot hole 50, the force which is necessary to implant the bone fixation tack 12 into the bone structure 52 is reduced as compared to if the entire body portion 18 had an equal radius. Due to the bone engagement areas 65 of fins 32, the surface area engaging the bone structure 52 in the pilot hole 50 is less than if the entirety of diameter F were filled with the bone fixation tack 12. Due to the presence of fins 32, only the area bounding the outside of the bone engagement area 65 engages pilot hole 50 during implantation of bone fixation tack 12. Therefore, the effective contact surface area of the bone fixation tack 12 is reduced due to the presence of fins 32 and the corresponding bone engagement areas 65. Thus, the force necessary to implant the bone fixation tack 12 is reduced when compared to a tack not including fins 32 and respective bone engagement areas 65.

Though the presence of fins 32 may decrease the surface area engaging the pilot hole, 50 during implantation, the holding force of the bone fixation tack 12 is not substantially reduced. Barbs 38 help ensure a strong and firm interaction of the bone fixation tack 12 and the bone structure 52. Not only do the fins 32 themselves engage the bone structure 52, but also the barbs 38 have additional surface area to engage the bone structure 52.

Both pull out and shear force tests were performed on a bone fixation tack according to the first embodiment of the present invention made formed according to the present invention of LactoSorb®, a material available from Biomet, Inc. in Warsaw, Ind., and trauma screws. As a result of these tests, it was found that bone fixation tack according to the present invention perform substantially as well as screws under similar conditions. Furthermore, the fact that the bone fixation tacks can be implanted approximately six times faster than trauma screws may greatly help in emergency situations. Additionally, the equivalency of the two systems can help ensure that the speediest alternative may be used without concern for the ability of the bone fixation tack to perform its task.

Figure 5:
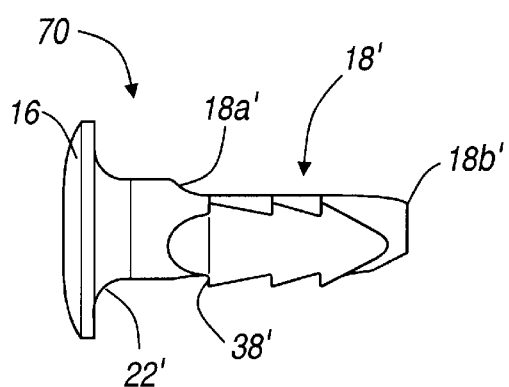
FIG. 5 is a side elevational view of a bone fixation tack according to a second embodiment of the present invention.

With reference to FIG. 5, a second embodiment of a bone fixation tack 70 is shown. Similar structures are given similar reference numerals here as described above in relation to the first embodiment augmented with a prime designation. According to the second embodiment of the second invention, a bone fixation tack 70 is substantially similar to the fixation tack 12 as described in the embodiment of the present invention. Bone fixation tack 70, however, does not include a break away hex 14 affixed to the head portion 16. However, bone fixation tack 70 does include a head portion 16' and a body portion 18'. Body portion 18' includes several portions also described above in relation to the first embodiment of the present invention and not repeated here. According to the second embodiment, a different driver would be necessary. However, overall bulk of bone fixation tack 70 is less than the first embodiment of the present invention and may reduce production costs. Furthermore, other types of devices may be used to implant bone fixation tack 70 by providing particular designs or detents in the head portion 16' of bone fixation tack 70.

Figure 6:
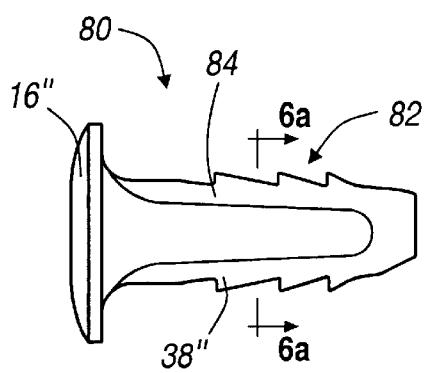
FIG. 6 is a side elevational view of a bone fixation tack according to a third embodiment of the present invention.
Figure 6A:
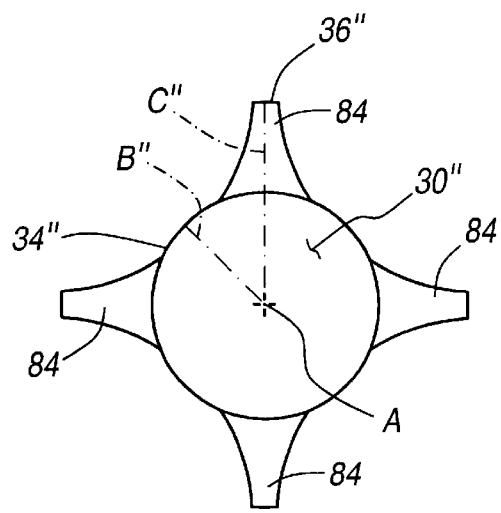
FIG. 6a is a cross-sectional view taken along lines 6a—6a of FIG. 6.

With reference to FIGS. 6 and 6a a bone fixation device 80, according to a third embodiment of the present invention is shown where similar portions are given similar numerals augmented by double primes as those described, in the first embodiment of the present invention. Bone fixation device 80 includes a head portion 16" and a body or body portion 82. The body portion 82 includes four fins 84 rather than three as illustrated in reference to a first embodiment of the present invention. The central region 30" includes a center point A" and a distance B" between the center point A" and an outside edge 34" of the center region 30". A distance C" between center point A" and outside 36" of fin 84 may be equal to distance C or may vary therefrom. Providing four fins 84 simply increases the surface area which, may engage a pilot hole formed in the bone structure. It will also be understood that additional fins may be formed on a bone fixation tack in a number greater than four as well without departing from the scope of the present invention. However, as a greater number of fins are added, there is a corresponding increase in implantation force.

The bone fixation tack of the present invention may be formed of several materials. One embodiment provides making the bone fixation tack from LactoSorb®, which is a bio-absorbable material, or other bio-absorbable material. LactoSorb® includes L-lactic acid and poly glycolic acid in combination to form a substantially solid material. The LactoSorb® or similar materials are absorbable into the body after the bone fixation tack has been implanted and the bone structure has had time to heal. However, it will be understood that bone fixation tack may be formed of any bio-compatible material including titanium, stainless steel, or other metal alloys that have sufficient strength and rigidity to hold a bone structure during healing.

The description of the invention is merely exemplary in nature and, thus, variations that do not depart from the gist of the invention are intended to be within the scope of the invention. Such variations are not to be regarded as. a departure from the spirit and scope of the invention.

What is claimed is:

1. A tack for fixation in bone, said tack comprising:
   a body portion having a proximal end and a distal end, adapted to be received in a bone structure;
   a head portion extending from said proximal end of said body portion;
   a shearable member shearably affixed to said head portion; and
   a projection having an exterior, and operatively associated with said body portion to form a bone engaging area, wherein said projection engages the bone structure to hold said body portion in the bone structure;
   a fin having an exterior, operably interconnecting said projection and said body portion, wherein said projection extends from said exterior of said fin.

2. The tack of claim 1, wherein said fin includes a plurality of said fins.

3. The tack of claim 2, wherein said body portion and said fins are integrally formed and have a generally triangular cross-section.

4. The tack of claim 1, wherein said fin and said body portion are integrally formed.

5. The tack of claim 1, wherein said body portion has a smaller circumference at said distal end when compared to said proximal end and has a generally tapered profile between said proximal end and said distal end.

6. The tack of claim 1, wherein said projection is a barb having a first end and a second end wherein said first end is near said proximal end and said first end is larger than said second end.

7. The tack of claim 1, wherein said shearable member has a substantially hexagonal cross section adapted to be received in a tool.

8. The tack of claim 1, wherein said body portion, said head portion, said shearable member, and said fin are all integrally formed.

9. The tack of claim 1, wherein said tack is made from a bio-compatible material selected from the group of a bio-absorbable material, a titanium, stainless steel, and a ceramic.

10. A surgical fixation tack for use in orthopedic surgery, said surgical fixation tack comprising:
    a tack portion having a first circumference, a proximal end, and a distal end;
    a head portion extending from lo said proximal end of said tack portion; and
    a plurality of fins extending from said tack portion extending a distance between said proximal end and said distal end, wherein said fins have a second circumference greater than said first circumference; and
    a member removably affixed to said head portion opposite said tack portion; and
    a projection, wherein said projection extends from at least one of said fins and is adapted to increase the holding cower of said at least one fin;
    wherein said tack portion, said head portion, said plurality of fins and said member are substantially integrally formed.

11. The surgical fixation tack of claim 10, wherein said member comprises a substantially hexagonal cross-section adapted to be received within a tool.

12. The surgical fixation tack of claim 10, wherein said tack portion has a smaller circumference at said distal end when compared to said proximal end and has a generally tapered profile between said proximal end and said distal end.

13. The surgical fixation tack of claim 10, wherein said at least one fin includes a plurality of said projections, wherein a profile of said of at least one fin is stepped.

14. The surgical fixation tack of claim 10, further comprising a body, wherein said tack portion is generally cylindrical and said fins project a distance from said tack portion to form said body.

15. The surgical fixation tack of claim 14, wherein said body has a generally triangular cross section.

16. The surgical fixation tack of claim 10, wherein said tack is formed of a bio-compatible material.

17. A surgical tack for orthopedic implant adapted to be held in a structure defining a bore having a bore circumference, said surgical tack comprising:
    a tack portion having a proximal end and a distal end and adapted to be held in the structure defining the bore;
    a plurality of fins extending from said lack portion;
    a head portion extending from said proximal end of said tack portion; and
    a projection extending radially from at least one of said plurality of fins, wherein said projection is adapted to hold said tack portion in the bore, wherein said projection is a barb having a first end and a second end wherein said first end is nearer said proximal end than said second end and said first end is larger than said second end.

18. The surgical tack of claim 17, wherein said tack portion includes an internal circumference and said fins form a first external circumference, wherein said first external circumference is adapted to be less than the bore circumference.

19. The surgical tack of claim 18, wherein said projection forms a second external circumference greater than said first external circumference, wherein said second external circumference is adapted to be greater than the bore circumference.

20. The surgical tack of claim 19, wherein said projection is integrally formed on said fin.

21. The surgical tack of claim 17, further comprising a removable member removably affixed to said head portion, wherein said removable member comprises a generally hexagonal cross section adapted to be received in a tool.

* * * * *

UNITED STATES PATENT AND TRADEMARK OFFICE
CERTIFICATE OF CORRECTION

PATENT NO. : 6,723,099 B1
DATED : April 20, 2004
INVENTOR(S) : David R. Goshert

It is certified that error appears in the above-identified patent and that said Letters Patent is hereby corrected as shown below:

Column 3,
Line 59, delete "a".

Column 5,
Line 29, delete "be".

Column 6,
Line 6, "tack" should read -- tacks --.

Column 7,
Line 52, delete "lo".

Column 8,
Line 3, "cower" should read -- power --.
Line 31, "lack" should read -- tack --.

Signed and Sealed this

Twenty-sixth Day of April, 2005

JON W. DUDAS
*Director of the United States Patent and Trademark Office*